US011504005B2

(12) United States Patent
Cannella et al.

(10) Patent No.: US 11,504,005 B2
(45) Date of Patent: Nov. 22, 2022

(54) DEVICE FOR DETECTING THE TACTILE SENSITIVITY OF A USER

(71) Applicants: Fondazione Istituto Italiano di Tecnologia, Genoa (IT); Universitá degli Studi di Genova, Genoa (IT)

(72) Inventors: Ferdinando Cannella, Genoa (IT); Maria Laura D'Angelo, Genoa (IT); Alessandro Chiolerio, Turin (IT)

( * ) Notice: Subject to any disclaimer, the term of this patent is extended or adjusted under 35 U.S.C. 154(b) by 635 days.

(21) Appl. No.: 16/603,234

(22) PCT Filed: Apr. 12, 2018

(86) PCT No.: PCT/IB2018/052575
§ 371 (c)(1),
(2) Date: Oct. 6, 2019

(87) PCT Pub. No.: WO2018/189715
PCT Pub. Date: Oct. 18, 2018

(65) Prior Publication Data
US 2020/0046292 A1      Feb. 13, 2020

(30) Foreign Application Priority Data
Apr. 14, 2017 (IT) .................. 102017000041851

(51) Int. Cl.
*A61B 5/00* (2006.01)
*A61B 90/00* (2016.01)
(52) U.S. Cl.
CPC .......... *A61B 5/0053* (2013.01); *A61B 5/4005* (2013.01); *A61B 5/4076* (2013.01);
(Continued)

(58) Field of Classification Search
CPC ......... A61B 5/16; A61B 5/165; A61B 5/4082; A61B 5/4088; A61B 5/168; A61B 5/162; A61B 5/4842; A61B 5/4035; A61B 5/375; A61B 5/4076; A61B 5/0048; A61B 5/486; A61B 5/44; A61B 5/441; A61B 5/442; A61B 5/0053; A61B 5/4005; A61B 5/4029; A61B 1/00055; A61B 2503/12;
(Continued)

(56) References Cited

PUBLICATIONS

Fischer, et al. "Tactile feedback for endoscopic surgery." Interactive technology and the new paradigm for healthcare: 114-117. (Year: 1995).*

(Continued)

*Primary Examiner* — David J. McCrosky
(74) *Attorney, Agent, or Firm* — Themis Law

(57) ABSTRACT

A device for detection of the tactile sensitivity of a user includes a base frame and a mechanical system joined to the base frame, the mechanical system being movable relative to the base frame and having a resting area for the fingertip of at least one finger of the user. The mechanical system includes a plurality of movable plate-shaped members arranged side by side to each other so that the resting area is defined by the thicknesses of at least part of the upper edges of the plate-shaped members. Each plate-shaped member is connected to an actuator, which can be operated to independently move each plate-shaped member from a minimum height position to a maximum height position, a control unit being further provided, which is adapted to operate the actuators.

10 Claims, 9 Drawing Sheets

(52) U.S. Cl.
CPC .......... *A61B 5/6826* (2013.01); *A61B 5/6843* (2013.01); *A61B 2090/064* (2016.02); *A61B 2562/0219* (2013.01); *A61B 2562/0247* (2013.01); *A61B 2562/16* (2013.01)

(58) Field of Classification Search
CPC .... A61B 34/76; G09B 21/003; G09B 21/004; G09B 21/005; G09B 21/007; A61H 2205/067; A61H 7/007
See application file for complete search history.

(56) References Cited

PUBLICATIONS

Cannella F et al: "Dynamic Investigation Test-rig on hAptics (DITA)", Journal of Physics: Conference Series, Institute of Physics Publishing, Bristol, GB, vol. 459, No. 1, Sep. 6, 2013 (Sep. 6, 2013), p. 12032, XP020250500, ISSN: 1742-6596, DOI: 10.1088/1742-6596/459/1/012032 Abstract; pp. 2,3; figures 1,2.

Justin H. Killebrew et al: "A dense array stimulator to generate arbitrary spatio-temporal tactile stimuli", Journal of Neuroscience Methods., vol. 161, No. 1, Mar. 1, 2007 (Mar. 1, 2007), pp. 62-74, XP055414947, NL ISSN: 0165-0270, DOI: 10.1016/j.jneumeth. 2006.10.012 Abstract; p. 3, paragraph 1—p. 7, paragraph 2; figures 1,2.

S. J. Bensmaia et al: "Temporal Factors in Tactile Spatial Acuity: Evidence for RA Interference in Fine Spatial Processing", Journal of Neurophysiology, vol. 95, No. 3, Mar. 1, 2006 (Mar. 1, 2006), pp. 1783-1791, XP055430641, US ISSN: 0022-3077, DOI: 10.1152/jn. 00878.2005 Abstract; p. 1784, col. 1, paragraph 7—col. 2, paragraph 1.

Bueno Marie-Ange et al: "Pile Surface Tactile Simulation: Role of the Slider Shape, Texture Close to Fingerprints, and the Joint Stiffness", Tribology Letters, Baltzer Science Publishiers, NL, vol. 59, No. 1, Jun. 13, 2015 (Jan. 13, 2015), pp. 1-12, XP035515038, ISSN: 1023-8883, DOI: 10.1007/S11249-015-0555-9 The whole document.

Michel Amberg et al: "STIMTAC", User Interface Software and Technology, ACM, 2 Penn Plaza, Suite 701 New York NY 10121-0701 USA, Oct. 16, 2011 (Oct. 16, 2011), pp. 7-8, XP058005907, DOI: 10.1145/2046396.2046401 ISBN: 978-1-4503-1014-7 The whole document.

\* cited by examiner

DEVICE FOR DETECTING THE TACTILE SENSITIVITY OF A USER

FIELD OF THE INVENTION

The present invention relates to a device for detection of the tactile sensitivity of a user.

The device comprises a base frame having a mechanical system attached thereto which can be moved relatively to the base frame and which has a resting area for the fingertip of at least one finger of the user.

BACKGROUND OF THE INVENTION

It is known that the sense of touch plays a key role in the behaviour of human beings: most interactions with the physical world occur through tactile sensations.

Indeed, human beings use their hands, particularly the fingertips, to explore the external environment for a variety of tasks ranging from simple recognition and grasping of objects up to complex palpation procedures.

When the surface of a fingertip contacts objects of various kinds, it is deformed.

As a result, the surface of the fingertip is subjected to a complex distribution of deforming forces which stimulate the mechanoreceptors of a user. The information obtained from such a stimulation is fundamental to assist various tasks such as recognizing objects, detecting the roughness of a surface, etc.

It is evident that investigating tactile sensitivity demands an ever-increasing attention not only for analysing the human behaviour but also in the field of robotics, where efficient tactile sensors are required to produce robotic fingers which can emulate human fingers.

In addition, the ability of detecting tactile sensitivity plays a key role in the evaluation of neurological diseases of the autonomic and peripheral nervous system.

This evaluation is performed by a method known in the art: the fingertip of the patient is moved along a resting area provided with reliefs to evaluate the spatial acuity of the fingertip skin.

Generally, such an approach includes using resting areas which can generate different tactile stimuli and interviewing the user in order to evaluate his/her tactile sensitivity.

A possible example of such a method as well as of a device for evaluating the tactile sensitivity is disclosed in document "Dynamic Investigation Test-rig on hAptics (DITA)", F. Cannella, L. Scalise, E. Olivieri, M. Memeo, D. G. Caldwell, Journal of Physics: Conference Series 459, 2013.

This document discloses a device for evaluating the tactile sensitivity, which comprises a resting area consisting of 17 different stimuli, each stimulus being associated to two reliefs separated by a flat surface.

One of the two reliefs has an identical wavelength for each grating, while the other relief has a specific wavelength for each grating.

The patient is instructed to slide his/her fingertip over the gratings in order to identify the different spatial frequencies thereof.

However, this device cannot customize the stimuli which are presented to the patient.

This limits the potential for analysing and studying patients because of the risk of detecting the tactile sensitivity of different patients in an approximate manner.

In order to overcome this drawback, document "A dense array stimulator to generate arbitrary spatio-temporal tactile stimuli", J. H. Killebrewa, S. J. Bensmaia, J. F. Dammann, P. Denchev, S. S. Hsiao, J. C. Craig, K. O. Johnson, J. Neurosc. Methods, 161(1):62-74, March 2007, discloses a system consisting of 400 pins arranged on a surface of about 1 $cm^2$ and independently moved by respective 400 motors controlled by a specific software tool which can generate a wide range of stimuli on the fingertip of a patient when the surface of the fingertip contacts said pins.

However, this approach is highly complex in design, especially from the mechanical point of view, with regards not only to the structural organization of the pins but also to the ability of moving them.

Accordingly, this approach has the clear disadvantages of complex and composite systems, such as high cost, high risk of breakage or malfunction, excessive size, and handling problems.

Therefore, there is a need—not satisfied by devices known in the art—for a device for detection of the tactile sensitivity of a user which overcomes the disadvantages as set forth above.

BRIEF SUMMARY OF THE INVENTION

Particularly, the invention aims to provide a device having a high accuracy in detection of neuronal diseases and neurodegenerative diseases, thereby allowing analyses to be carried out in a fast, efficient and repeatable manner.

In addition, an object of the invention is to provide a device which is simple in design and which can be used not only for scientific investigations but also as a non-invasive tool for diagnosing and controlling diseases of the peripheral nervous system for clinical purposes.

The present invention achieves the above objects by providing a device for detection of the tactile sensitivity of a user as described above, in which the mechanical system comprises a plurality of movable plate-shaped members which are arranged side by side to each other in such a way that the resting area is defined by the thicknesses of at least part of the upper edges of the plate-shaped members.

Furthermore, each plate-shaped member is connected to an actuator which can be operated to independently move each plate-shaped member from a minimum height position to a maximum height position.

Finally, a control unit is provided which is adapted to operate the actuators.

Since the plate-shaped members can be independently moved under the control of the control unit, a wide range of stimuli can be generated for transmission to the user.

In particular, the plate-shaped design of the mechanical system can achieve the best compromise between design simplicity and ability to generate a high range of tactile stimuli.

As will become more apparent from the description of certain exemplary embodiments, each stimulus may have a sine-shaped profile whose spatial/temporal frequencies, amplitude and duration can be changed.

This results in an improved resolution when the tactile sensitivity of different users is evaluated.

Advantageously, such a configuration provides an increased variety of stimuli available with the use of a single set of movable members, thereby assuring an increased accuracy of the procedures and thus saving time.

The features described immediately below are intended to further facilitate not only the design process but also the use of the device of the present invention.

According to a first embodiment, each plate-shaped member is connected to a corresponding actuator through a lever which is attached to one end of the plate-shaped member.

In addition, each plate-shaped member is hinged at the other end in such a way that the transition from the minimum height position to the maximum height position occurs when the plate-shaped member is rotated, particularly about the hinged end thereof.

Since the plate-shaped members can be vertically moved by a corresponding lever, this results in a device which can measure the tactile sensitivity while being compact in size and portable.

Furthermore, in order to differentiate and define the resting area, a variant embodiment provides that each plate-shaped member has an edge projecting from the upper edge thereof at the resting area towards the fingertip of the user.

Thus, the resting area is elevated with respect to the upper edges of the plate-shaped members, and it is defined by the set of projecting edges of each plate-shaped member.

It will be appreciated that, when stimuli are generated, the plate-shaped members are rotated through very small angles and, therefore, the rotation thereof is perceived by the user as a translation of each plate-shaped member towards the fingertip.

Such a consideration is particularly important because, in this way, the above-described design simplicity can be kept without negatively affecting the quality of the generated stimuli and the quality of the analyses to be carried out.

According to a preferred embodiment, the mechanical system comprises a slider adapted to slide the mechanical system with respect to the base frame.

A drive unit is also provided for driving the slider.

The actuation of the slider results in a movement of the mechanical system which activates the proprioception system of the user.

As long as the hand and particularly the fingertip of the user are maintained in contact with the mechanical system, a movement of the mechanical system rotates the joints of the shoulder and arm, thereby activating the proprioception system of the user.

As will become more evident from the exemplary embodiments illustrated and described hereinbelow, the fingertip is always in contact with the same plate-shaped members, even when the slider is driven.

When the slider is driven, the forearm of the user is moved, the proprioception system is activated and a different input is provided which suggests to the user that he/she is exploring not just a point but a surface, thereby allowing for evaluations which are not only punctual but also superficial in nature.

Therefore, the device of the present invention can evaluate both the tactile sensitivity and the proprioceptive system of a user.

As a result, the device of the present invention can also be used with patients suffering from neurodegenerative diseases such as, for example, Parkinson's disease.

According to a preferred embodiment, the plate-shaped members are made of different metal materials, particularly, two metal materials are used in such a way that each plate-shaped member made of one metal material is adjacent to and in contact with plate-shaped members made of the other metal material.

Advantageously, brass and steel are used.

The use of two different metal materials can limit the friction between the plate-shaped members, thereby reducing the wear thereof as well as the risk of failure for the mechanical system.

Advantageously, said actuators are divided in two groups which are arranged on opposite sides with respect to the plurality of plate-shaped members.

As will be illustrated hereinbelow, this variant embodiment allows the overall dimensions of the device of the present invention to be reduced while keeping design parameters constant in order to facilitate the handling of the plate-shaped members by the control unit.

As previously anticipated, such a distribution of the actuators contributes to further reduce the size of the device of the present invention for portability purposes.

According to an embodiment, the device of the present invention comprises a system for detecting the pressure applied by the fingertip of the user.

Preferably, the pressure detection system comprises a pressure sensor positioned on the upper edge of each plate-shaped member at the resting area, and an acquisition unit connected to each pressure sensor.

Preferably, the pressure detection system comprises one acquisition unit which is connected to all the pressure sensors.

In this case, a parallel-channel device or multiplexer can be provided for connection.

Such a configuration is particularly advantageous because it further improves the evaluation of tactile sensitivity of the user.

In fact, the user can perceive the difference among different stimuli either by just touching the resting area, which indicates a high sensitivity, or by pressing the fingertip against the resting area, which indicates a low sensitivity.

Advantageously, the pressure sensor can read the distribution of the pressure applied by the user.

Furthermore, the pressure sensor can be used to check that the fingertip of the patient is appropriately placed on the resting area.

It will be appreciated that any pressure sensor known in the art can be used.

According to an improvement, a piezoresistive sensor can be provided.

An example of such a sensor is disclosed in document "A tactile sensor device exploiting the tunable sensitivity of copper-PDMS piezoresistive composite", S. Stassi, G. Canavese, F. Cosiansi, R. Gazia, M. Cocuzza, Procedia Engineering 47 (2012) 659-663, the contents of which should be considered as an integral part of the present specification.

According to a further embodiment, the control unit is a remote unit which controls a microcontroller connected to the actuators.

In particular, the remote unit generates command signals adapted to set the height of each plate-shaped member, and the microcontroller comprises means for detecting the height of each plate-shaped member.

The control unit can create different control signals, preferably in the form of sine waves, by changing the duration and amplitude of a stimulus as well as the spatial and temporal frequencies thereof.

Randomly combining such stimuli allows the tactile sensitivity of the user to be measured.

Therefore, this makes it possible to optimally investigate the tactile sensitivity of each user by stimulating the surface of the fingertip in order to activate the mechanoreceptors.

Thus, the control unit generates sinusoids which are transformed into mechanical movements: the profile of each sinusoid indicates a different height for each plate-shaped member.

From the preceding description it becomes clear that the structural characteristics of the device of the present invention allow the tactile sensitivity of a user to be evaluated by simultaneously measuring different parameters in a precise and systematic manner, which results in a high level of accuracy.

In addition, according to the peculiar embodiments described herein, a device for the detection of the tactile sensitivity of a user is provided which is compact in size and which makes use of plate-shaped members which can be moved both vertically and horizontally to detect the tactile sensitivity of the user and measure the pressure applied by the fingertip of the user in a reliable manner.

These and other features and advantages of the present invention will become more fully apparent from the following description of certain non-limiting exemplary embodiments illustrated in the accompanying drawings, wherein:

DETAILED DESCRIPTION OF THE INVENTION

It will be appreciated that the figures accompanying the present patent application are included in order to better understand the advantages and features of the device of the present invention.

Thus, these embodiments are intended to be merely illustrative and are not intended to limit the scope of the inventive concept of the present invention, which is to provide a device for detection of the tactile sensitivity of a user which allows measurements and evaluations to be carried out with a high degree of accuracy while keeping the components of the device simple in design.

Figure 1A:
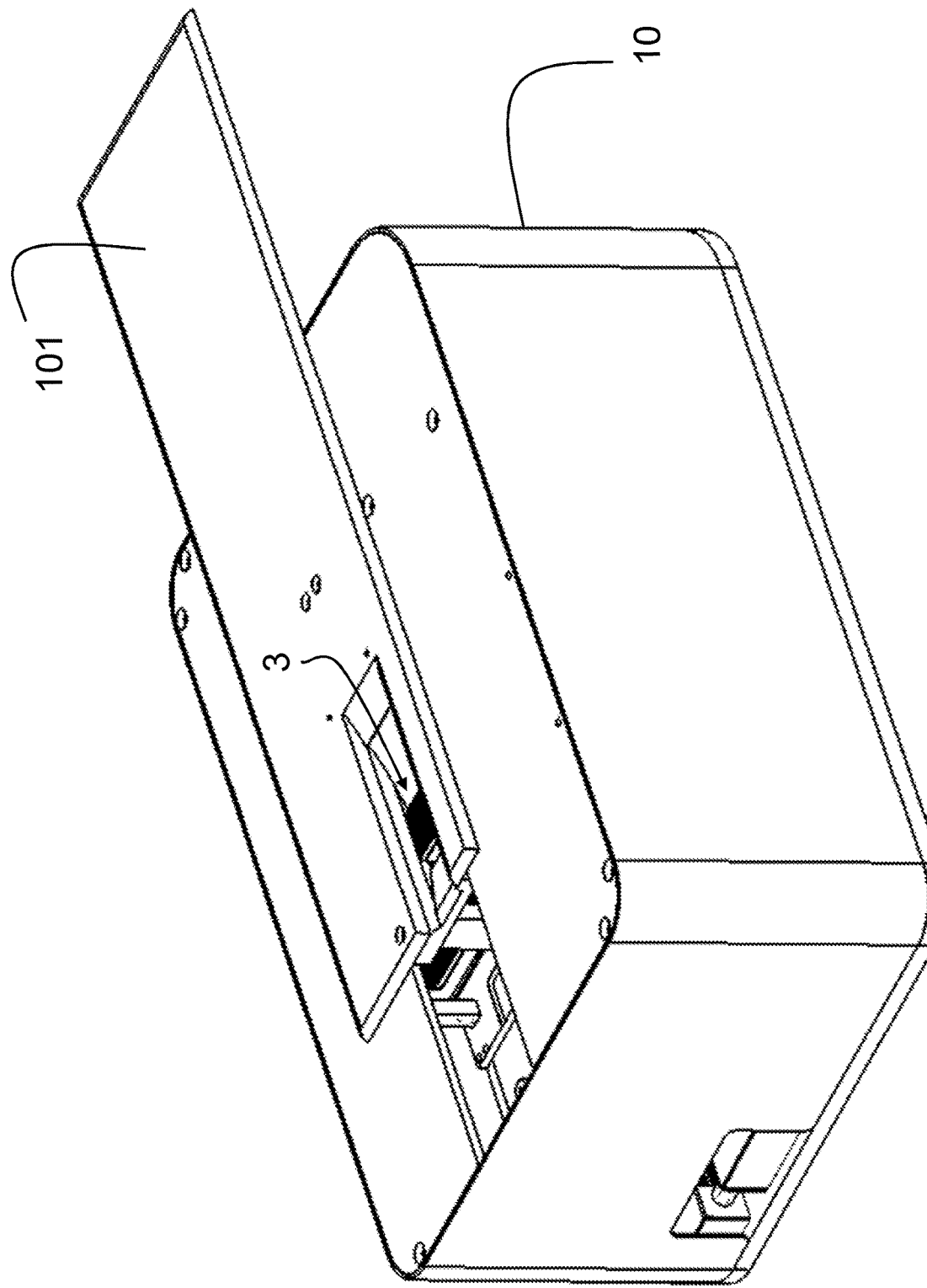
FIGS. 1a and 1b illustrate two views of the device of the present invention according to a possible embodiment.
Figure 1B:
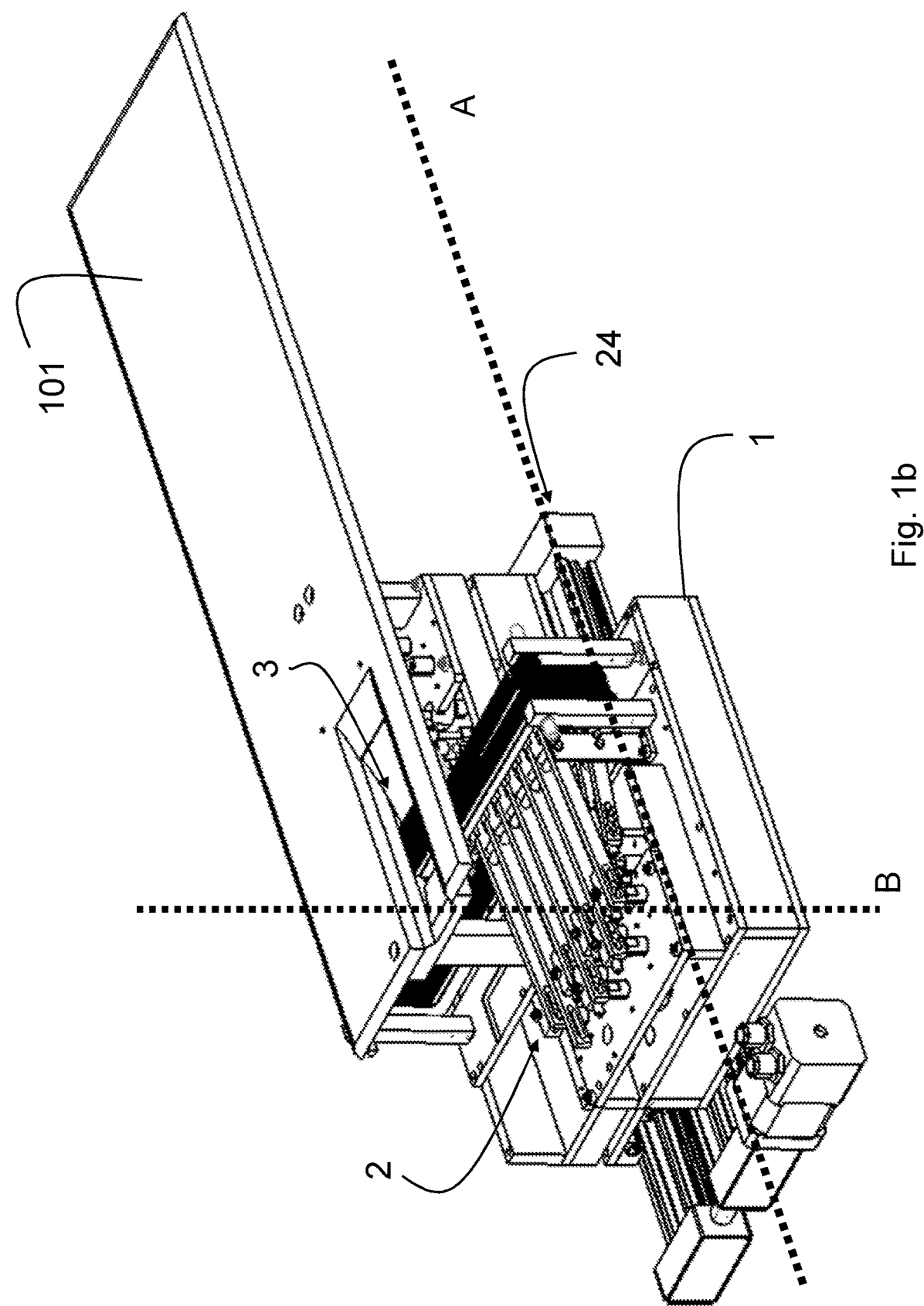

FIGS. 1a and 1b illustrate a first embodiment of the device of the present invention, respectively in a version with an external covering case 10 and without the external case.

According to the embodiment illustrated in the Figures, the device for detection of the tactile sensitivity of a user comprises a base frame 1 and a mechanical system 2 attached to the base frame 1.

As can be seen particularly in FIG. 1b, the mechanical system 2 can be moved relatively to the base frame 1, and it comprises a resting area 3 for at least one fingertip of a user.

In use, the user rests the palm of his/her hand on a platform 101 in such a way that one of his/her fingertips, preferably the fingertip of his/her index finger, is in contact with the resting area 3.

The mechanical system 2 comprises a plurality of movable plate-shaped members 21 arranged side by side to each other in such a way that the resting area 3 is defined by the thicknesses of at least part of the upper edges of the plate-shaped members 21.

Figure 2A:
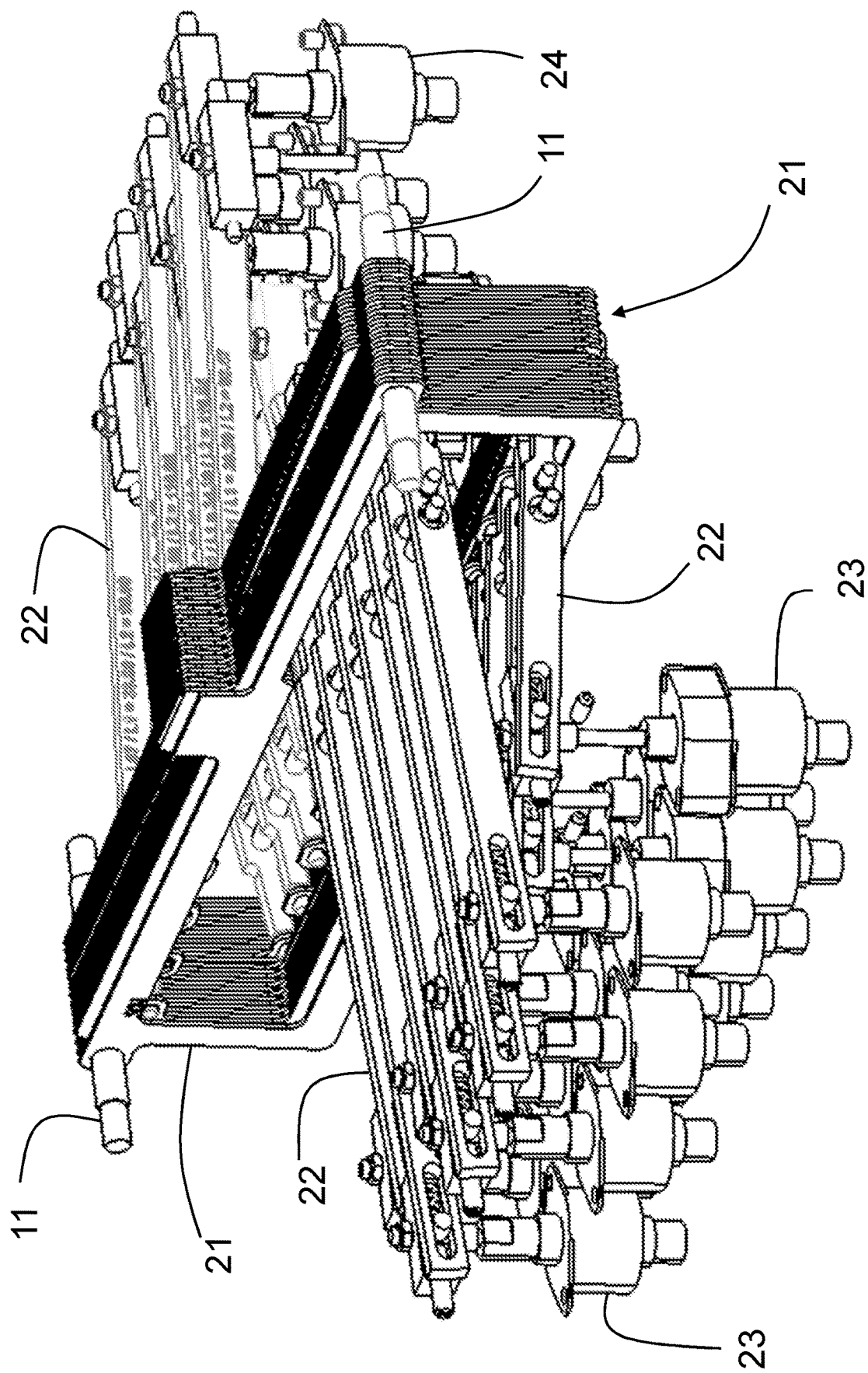
FIGS. 2a and 2b illustrate the mechanical system of the device of the present invention.
Figure 2B:
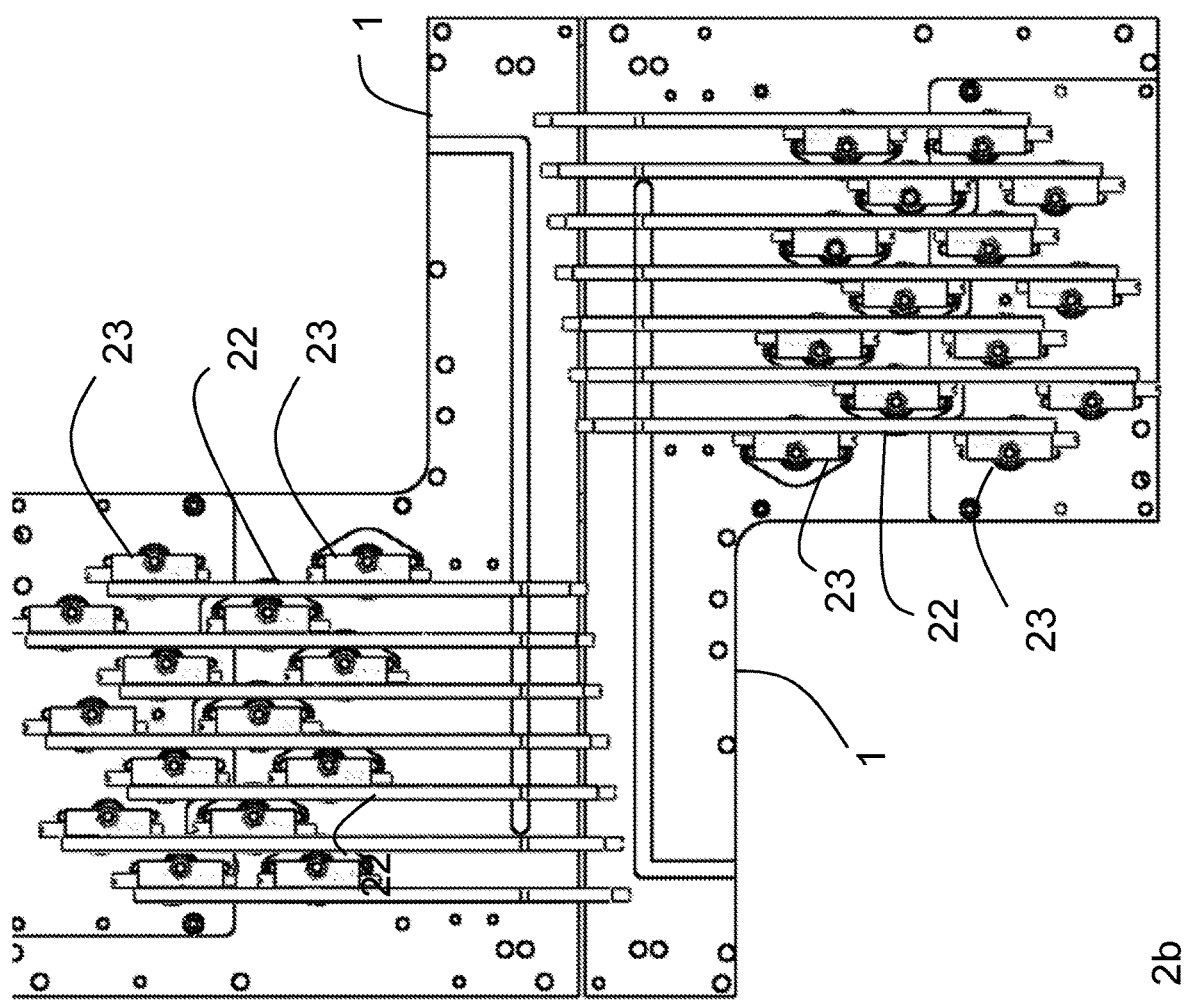
Figure 3A:
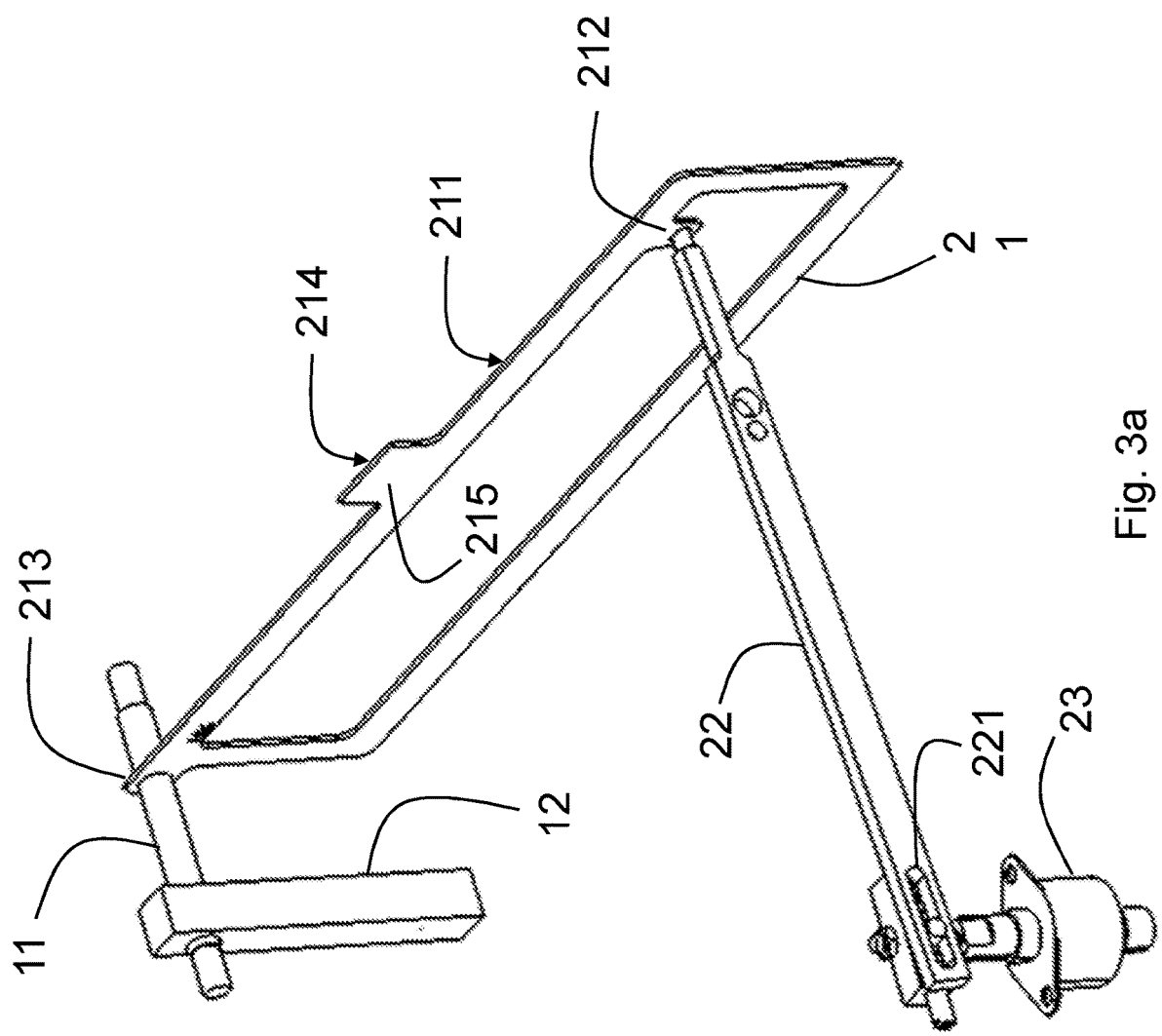
FIGS. 3a, 3b and 4 illustrate certain details of the mechanical system of the device of the present invention.
Figure 3B:
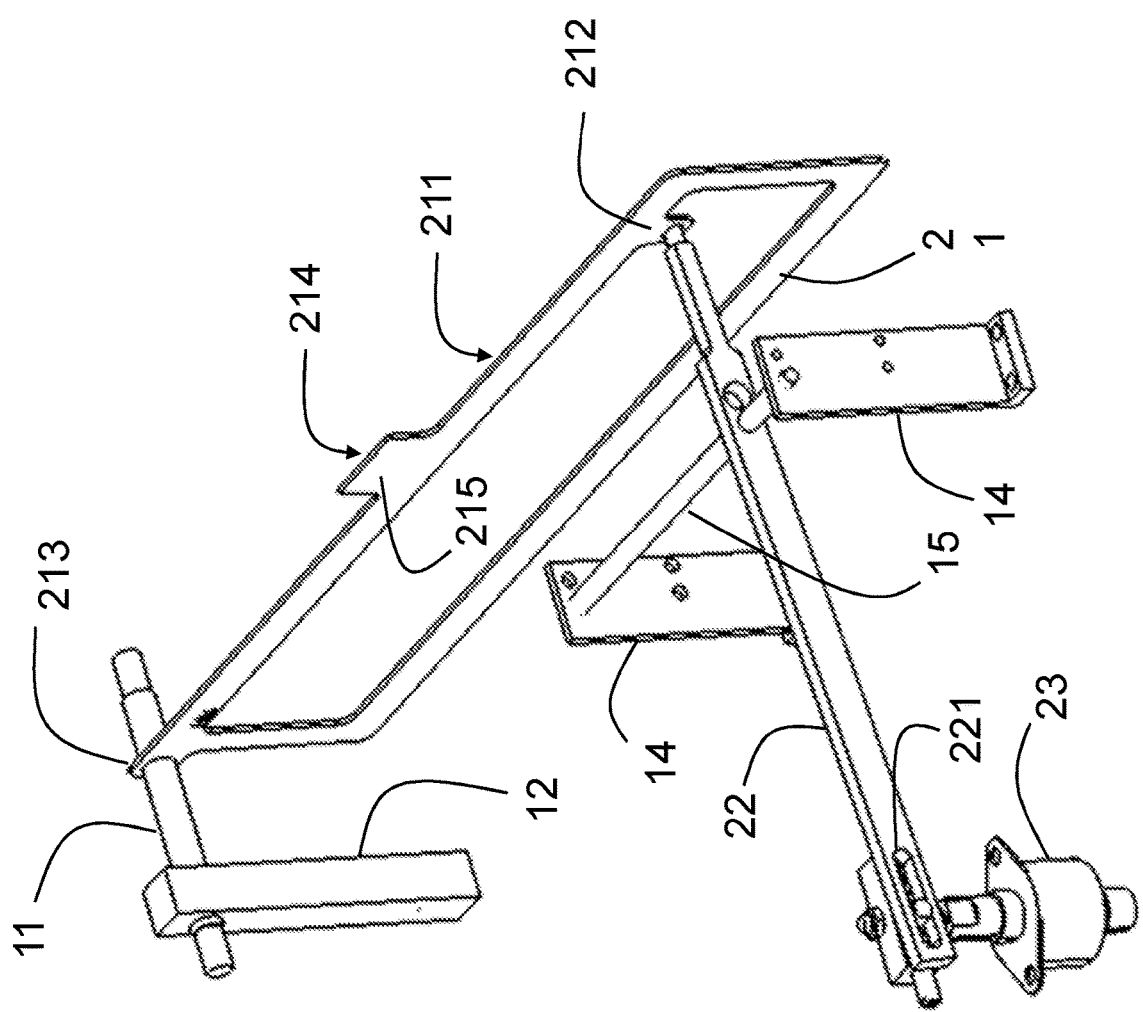

As is clear from FIGS. 2a and 2b, the mechanical system 2 consists of a plurality of modular assemblies attached to each other, two embodiments of such assemblies being illustrated in FIGS. 3a and 3b.

Each modular assembly consists of a plate-shaped member 21, a lever 22 and an actuator 23.

It is clear that, when each actuator 23 is operated, the respective plate-shaped member 21 is independently moved through the lever 22 from a minimum height position to a maximum height position.

As will be seen hereinbelow, since each plate-shaped member 21 can be moved independently, the plate-shaped members 21 can be positioned at different heights so as to generate specific stimuli on the surface of the fingertip of the user.

Indeed, the envelope along the line joining the upper edges 211 of the plate-shaped members 21 defines a precise form which is changed according to the stimulus to be obtained.

There is provided a control unit—described in detail hereinbelow—which is adapted to generate control signals for the operation of the actuators 23 in order to create tactile stimuli on the fingertip of the user.

With particular reference to FIGS. 3a and 3b, the plate-shaped member 21 is connected to the corresponding actuator 23 through the lever 22 at an end 212 of the plate-shaped member 21.

According to the illustrated embodiment, the end 212 has an appropriate eyelet which receives the end pin of the lever 22.

In addition, the plate-shaped member 21 is hinged at an end 213 in such a way that the transition from the minimum height position to the maximum height position occurs when the plate-shaped member 21 is rotated about the end 213.

According to the embodiment illustrated in FIGS. 3a and 3b, the end 213 has an eyelet for receiving a pin 11 supported by a pillar 12, both integral with the base frame 1, in such a way as to ensure the rotation thereof about the pin 11 received within the eyelet when the plate-shaped members are moved.

The levers 22 can be attached to the actuators 23 through an attachment means of the actuator 23 which engages a slot 221 to adjust the arm of the lever 22 in length.

Further with particular reference to FIGS. 3a and 3b, each plate-shaped member 21 has an edge 214 projecting from the upper edge 211 at the resting area 3 towards the fingertip of the user.

As illustrated, the upper portion of the plate-shaped member 21 extending towards the fingertip provides an appendix 215 having a projecting edge 214 in such a way that the resting area 3 is defined by the set of projecting edges 214 of each plate-shaped member 21.

According to the embodiment illustrated in FIG. 3a, the plate-shaped member 21 is moved in the same direction as the actuator 23, meaning that, when the actuator is operated to be moved upward, the end 212 is also moved upward.

In contrast, FIG. 3b illustrates a preferred and particularly advantageous embodiment: the lever 22 has at least one hole for receiving a pivot member 15 supported by two support members 14.

The support members 14 and the pivot member 15 are integral with the base frame 1 in such a way that, when the actuator 23 is operated to be moved upward, the end 212 of the plate-shaped member 21 is moved downward in the opposite direction.

With particular reference to the variant embodiment illustrated in FIG. 2a, there are provided 28 plate-shaped members 21, each being 1 millimeter in thickness so that the resting area 3 is 28 millimeters in length.

In addition, the plate-shaped members include plate-shaped members made of steel and plate-shaped members made of brass which are arranged alternately with each other in order to reduce friction when they are moved.

Particularly, FIGS. 2a and 2b illustrate the unique arrangement for actuators 23, levers 22 and plate-shaped members 21.

In order to minimize size and footprint and simultaneously provide each plate-shaped member 21 with an identical lever linkage arrangement, the actuators 23 are divided in two groups arranged at opposite sides with respect to the plurality of plate-shaped members 21.

Furthermore, the actuators 23 in each group are arranged on two planes at different heights in such a way that the levers 22 of the actuators 23 lying on the upper plane are connected from above to each plate-shaped member 21 while the levers 22 of the actuators 23 lying on the lower plane are connected from below to each plate-shaped member 21.

At the same time, the plate-shaped members 21 are arranged alternately with each other, i.e. the plate-shaped members in odd positions are driven by the group of actuators 23 on either the right side or the left side with reference to FIG. 2a while the plate-shaped members in even positions are driven by the other group of actuators 23.

In this way, if the proximal pin 11 in FIG. 2a engages the eyelets of the plate-shaped members 21 in even positions, then the distal pin 11 in FIG. 2a engages the eyelets of the plate-shaped members 21 in odd positions, or vice versa.

Such a configuration is further elucidated in FIG. 2b, which illustrates a top view of the mechanical system 2 with the plate-shaped members 21 being omitted.

From FIG. 2b, it is possible to appreciate the particular arrangement of the actuators 23 in order to minimize the footprint thereof to the maximum extent feasible.

As already anticipated in FIG. 2a, the levers 22 are arranged on an upper plane and a lower plane and, consequently, in case 28 levers are used, there are provided 14 pairs of levers with a common vertical plane.

Figure 4:
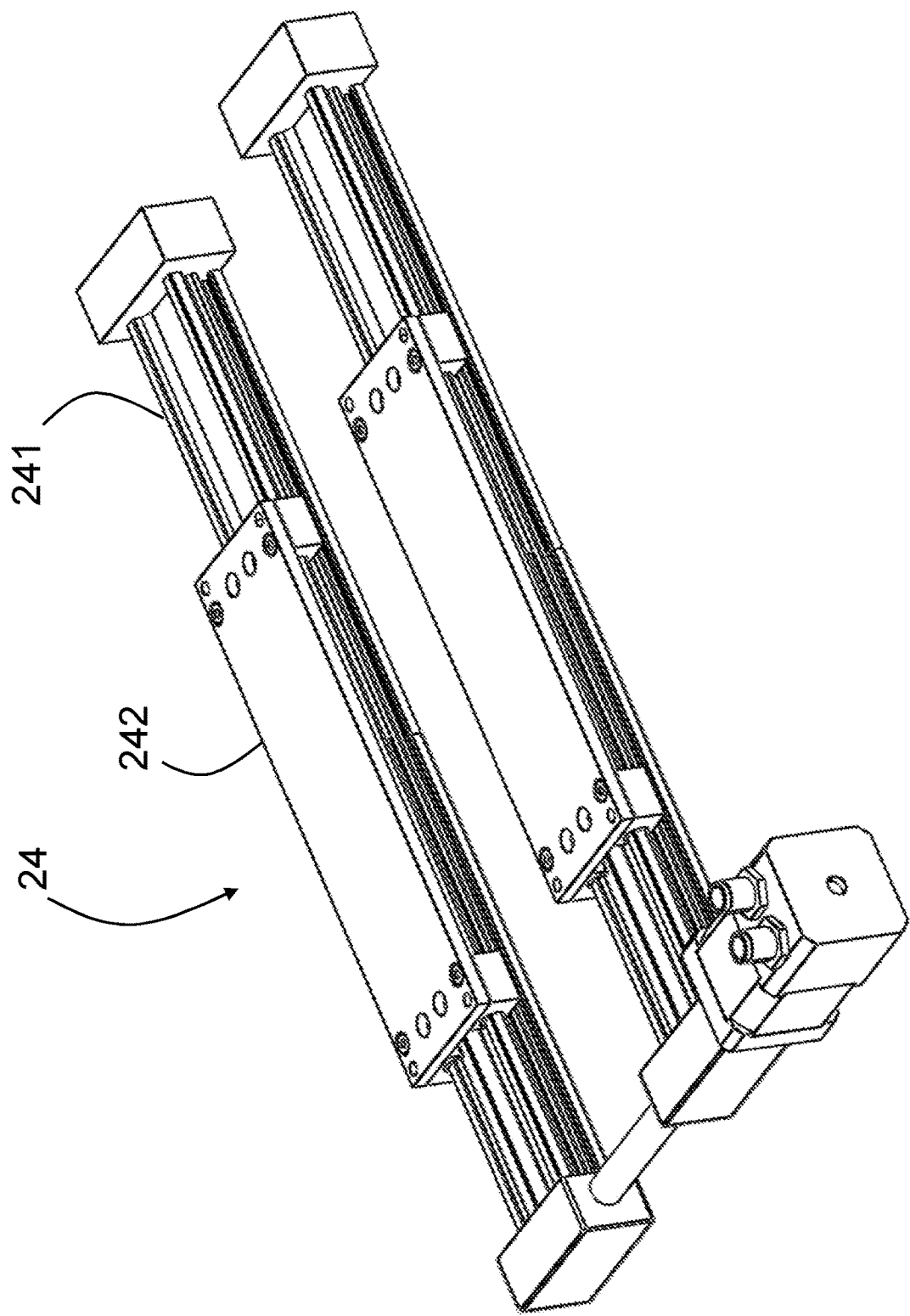

With particular reference to FIGS. 1b and 4, the mechanical system 2 comprises a slider 24 adapted to slide the mechanical system 2 with respect to the base frame 1.

Thus, the mechanical system 2 has two types of movement: a vertical movement of each plate-shaped member 21, particularly along axis B, and a longitudinal movement of the entire mechanical system 2 relatively to the base frame 1 as indicated by axis A.

The slider system is driven by a corresponding drive unit which is not illustrated in the figures.

For example, the slider system can consist of a guide 241 integral with the base frame 1 and a slide 242 integral with the mechanical system.

With particular reference to FIG. 4, there are provided two guides 241 and two slides 242: the stroke of the slides along the guides is about 500 millimeters in length.

Preferably, only one slide 242 is driven by a drive unit, while the other slide can be connected to the active slide through a rigid arm.

With reference to FIGS. 1a to 4, it will be appreciated that the fingertip of the user in contact with the resting area 3 remains in contact with the set of plate-shaped members 21 even when the mechanical system 2 is moved along axis A.

Figure 5:
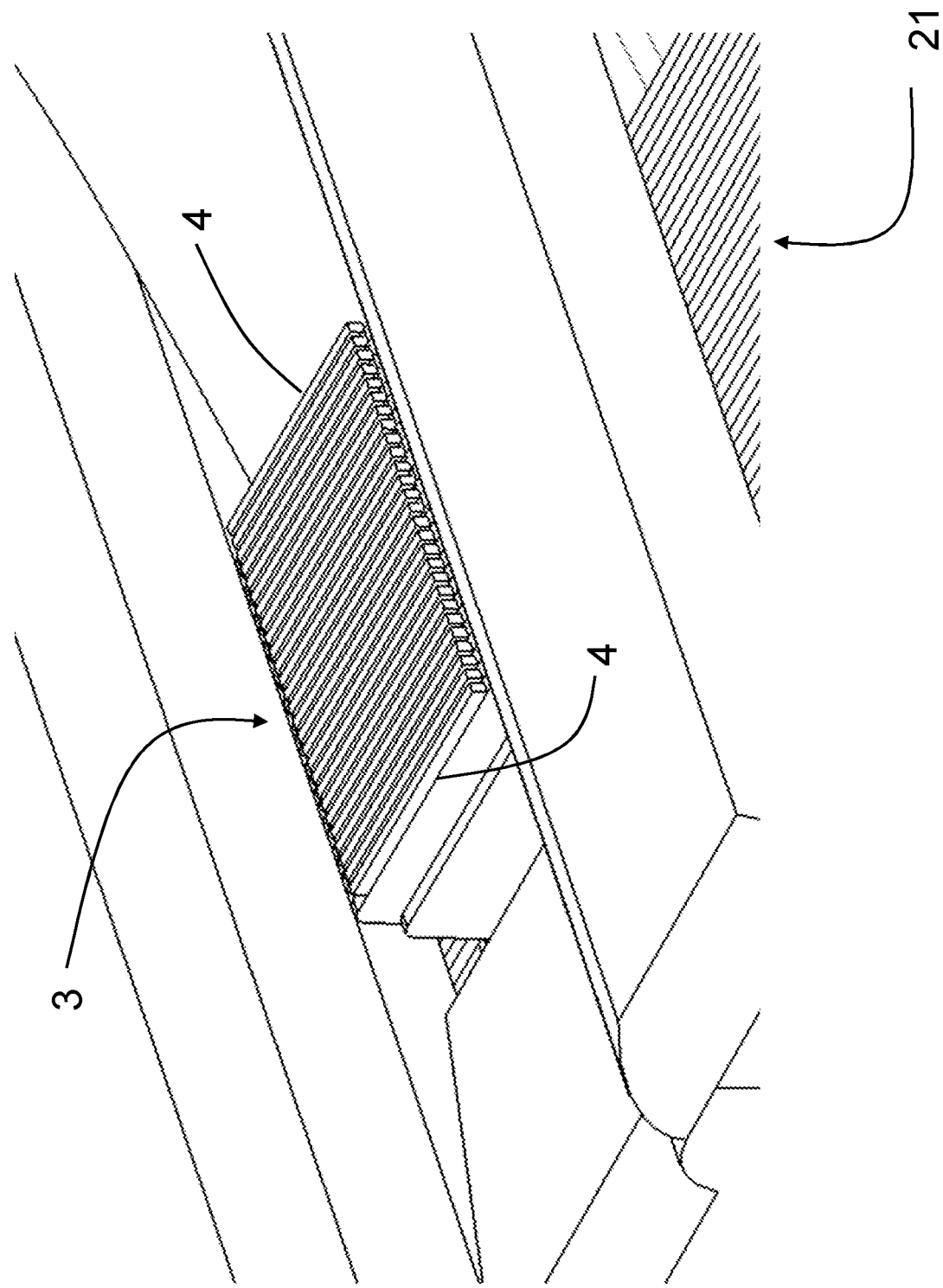
FIG. 5 illustrates a concept diagram of the pressure sensor of the device of the present invention.

According to a preferred embodiment as illustrated in FIG. 5, the device of the present invention provides a system for detecting the pressure applied by the fingertip of the user.

The detection system comprises a pressure sensor, particularly a piezoresistive sensor 4, which is positioned on the projecting edge 214 of each plate-shaped member 21, and an acquisition unit—not illustrated in the figure—which is connected to each piezoresistive sensor 4.

As illustrated in FIG. 5, the piezoresistive sensors 4 are arranged in such a way to almost completely cover the resting area 3 in order to appropriately read the pressure distribution on the surface of the fingertip in contact with the resting area 3.

According to a possible embodiment, the sensor 4 comprises a layer of a rigid material which is attached to the projecting edge 214 of each plate-shaped member 21, the rigid layer having a plurality of electrodes deposited thereon, and a layer of a nanocomposite material with piezoresistive features.

Specifically, the nanocomposite material comprises an insulating polymeric matrix containing a plurality of electrically conductive elements as a dispersion.

Preferably, the rigid layer may consist of a layer of monocrystalline silicon or a layer of Kapton.

The use of Kapton makes easy to connect the sensor 4 with any acquisition unit.

For example, the layer of nanocomposite material may consist of an epoxy resin or acrylic resin which contains a dispersion of conductive elements with sharp corners, such as nano-tubes of carbon or nano-particles of gold, copper, silver, nickel, preferably wherein each particle is provided with nano-tips, such particles being known as a "spiky nano-particles".

As is known, this configuration is such that a pressure applied by the fingertip to the sensors 4 changes the distribution of the insulating spaces interposed among the conductive elements, thereby changing the specific electrical resistance and capacitance of the sensor 4 by either the tunnelling effect or a direct contact among the conductive elements, a phenomenon known as percolation.

Such resistivity changes can be recorded by the acquisition unit in order to convert them into pressure values.

In order to maximize the accuracy of the parameters detected by the sensor, the acquisition unit may comprise a resonant circuit which can be connected to the sensor 4 by means of metal foils. In fact, as a pressure applied to the nano-composite changes not only the resistive component but also the reactive component (the sum of which components represents the complex impedance), whether it is capacitive or inductive in nature, the frequency of a resonant circuit changes in a manner which can be directly correlated to the pressure change as described in document "A Robust Capacitive Digital Read-Out Circuit for a Scalable Tactile Skin", A. Damilano, P. Motto Ros, A. Sanginario, A. Chiolerio, S. Bocchini, I. Roppolo, C. F. Pirri, S. Carrara, D. Demarchi, M. Crepaldi, IEEE Sensors Journal 2017 (in press) DOI: 10.1109/JSEN.2017.2681065, the contents of which should be considered as an integral part of the present specification.

According to this embodiment, for each sensor 4, the upper surface of the layer of monocrystalline silicon may not be completely covered by the nano-composite material: therefore, the metal foils can be arranged on the "bare" portion of silicon and then welded or connected to wires by means of conductive resins for the connection with the acquisition unit.

As anticipated, the independent movement of the plate-shaped members 21 is controlled by a control unit which is connected to the electronics—not illustrated in the figures—of the actuators 23.

The control unit generates control signals adapted to set the height of each individual plate-shaped member 21 in order to generate stimuli on the surface of the fingertip of the user in contact with the resting area 3.

Advantageously, the control unit consists of a remote unit 5 which controls a microcontroller connected to the actuators 23 and which comprises means for detecting the height of each plate-shaped member 21.

Preferably, the microcontroller comprises one or more control units which can check the status of a group of actuators.

According to this configuration, the microcontroller is responsible for the activities performed in real-time mode, while the remote unit is responsible for the activities performed in non-real-time mode.

By way of an example, in an embodiment, the microcontroller may be a 12V-powered BeagleBone Black-type board.

The board may incorporate a DAQ NI-type data acquisition system and a hardware device for the connection and control of the actuators 23.

The board may comprise a logic program designed to handle the state of each actuator 23, particularly the number of steps, the direction of operation and the operation thereof.

According to an exemplary embodiment, the control unit of the microprocessor is interfaced with the data acquisition system. The microcontroller handling logic program is designed to move the actuators 23 in a consecutive manner and to assign the direction of movement and the number of steps to be performed to each actuator.

According to a further embodiment, the control units of the microprocessor comprise 8-bit flip-flop-type electronic circuits.

Since each flip-flop can handle four different actuators 23, if there are 28 actuators, then 7 flip-flops are required.

The microcontroller handling logic program is designed to set the status of the actuators 23 handled by the first flip-flop and then alternately operate each flip-flop by turning on the first flip-flop, then turning off the first flip-flop and turning on the second flip-flop, etc., in order to transfer all information related to the states of each actuator 23.

At this point, the control signal can be generated, preferably by the remote unit through a control signal generating algorithm, in order to set the heights of each actuator 23.

It is evident that the configuration described just above allows the actuators 23 to be synchronously and readily moved by sending a single control signal, without having to control each plate-shaped member 21 separately.

In fact, the plate-shaped members 21 are mechanically synchronized by using a single control signal.

According to a possible embodiment, the remote unit may be connected to both the microcontroller and the drive unit for the slider 24 so as to handle simultaneously both the stimuli to be presented to the fingertip and the proprioceptive system of the user.

Preferably, the control signal sets the various heights of the plate-shaped members 21 so as to generate a sine wave-shaped profile along the longitudinal axis of the device of the present invention.

As anticipated, the sine wave can be changed in temporal frequency, spatial frequency and amplitude according to the stimulus to be generated.

Figure 6:
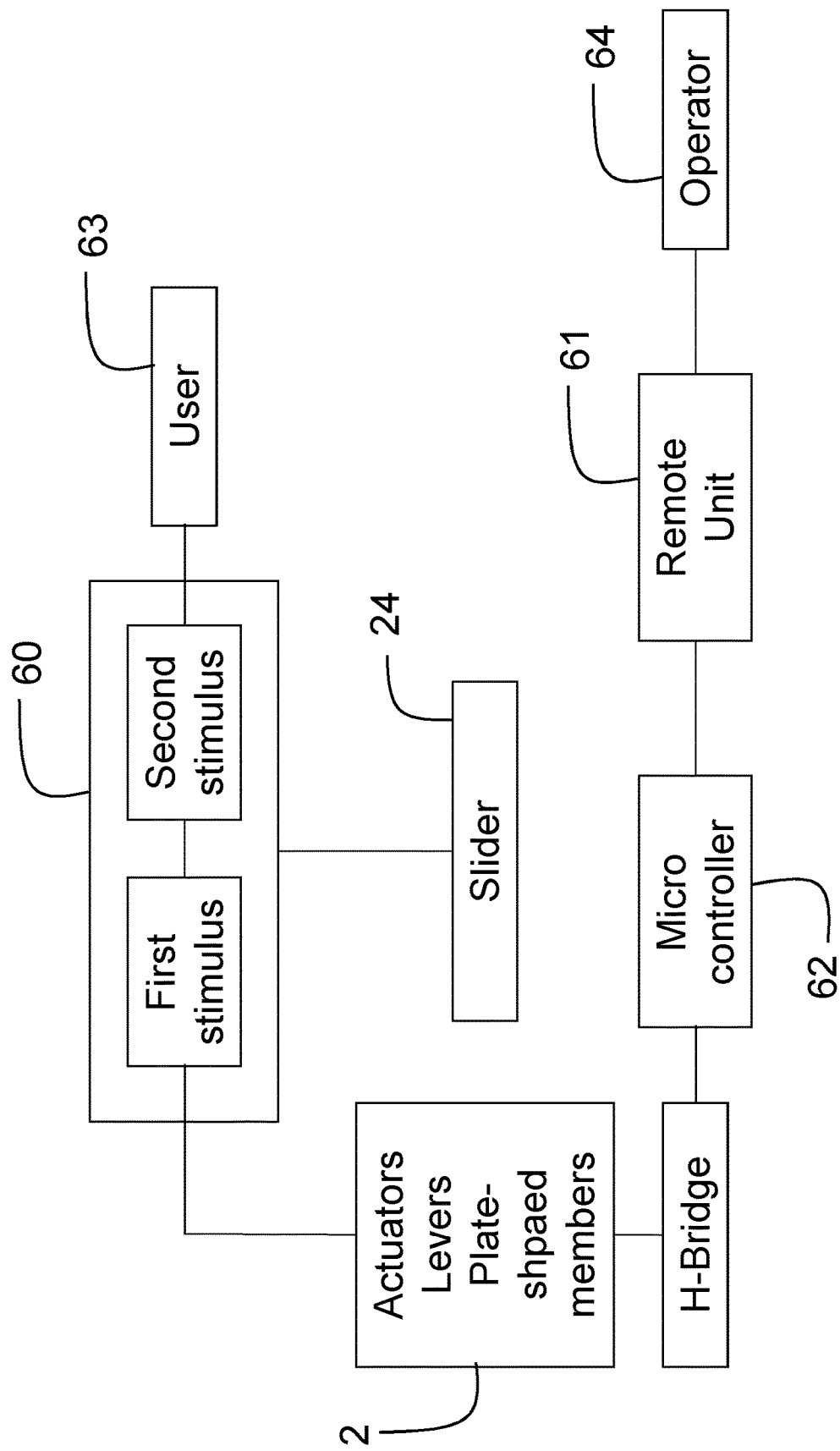
FIG. 6 illustrates a functional diagram of the operation of the device of the present invention.

Having described the characteristics of the device of the present invention, FIG. 6 illustrates a concept diagram showing a possible use of the device.

The user contacts the resting area 3 with the fingertip of his/her right index finger.

Then, the user is acoustically and visually isolated by means of a set of headphones and a blackout eye mask.

Each trial 60 consists of two different stimuli to which the user is subjected.

The remote unit 61 sends a control signal to the microcontroller 62 in order to generate the first stimulus.

The microcontroller 62 sets the mechanical system 2 according to the above-described methodology, thereby operating the actuators and levers and setting the heights of the plate-shaped members so as to match the profile of the selected form and send the stimulus to the fingertip in contact with the plate-shaped members (in the presence or absence of the pressure sensor 4).

Then, the remote unit 61 sends a further control signal in order to generate the second stimulus.

Once the trial 60 is completed, the user 63 indicates which stimulus was perceived with the greatest spatial frequency to the operator 64, and the operator 64 creates a document with all the responses of the various users for any necessary evaluations.

Finally, each trial 60 can include an interaction with the slider 24 in order to activate the proprioceptive system of the user 63.

The invention claimed is:

1. A device for detection of tactile sensitivity of a user, comprising:
   a base frame (1); and
   a mechanical system (2) joined to said base frame (1), said mechanical system (2) being movable relatively to said base frame (1), said mechanical system (2) having a resting area (3) for a fingertip of at least one finger of said user,
   wherein said mechanical system (2) comprises a plurality of movable plate-shaped members (21) arranged side by side to each other so that said resting area (3) is defined by thicknesses of at least some upper edges (211) of the plate-shaped members (21), and
   wherein each plate-shaped member (21) is connected to a respective actuator (23) adapted to be operated to independently move each plate-shaped member (21) from a minimum height position to a maximum height position;
   a control unit being further provided which is adapted to operate said actuators (23).

2. The device according to claim 1, wherein each plate-shaped member (21) is connected to the respective actuator (23) through a lever (22), said lever (22) is-being attached to a first end (212) of said plate-shaped member (21), said plate-shaped member (21) being hinged at a second end (213) so that a transition from the minimum height position to the maximum height position occurs when said plate-shaped member (21) is rotated about said second end (213).

3. The device according to claim 1, wherein each plate-shaped member (21) has a projecting edge (214) projecting from said upper edge (211) at said resting area (3) towards the fingertip of said user in such a way that the resting area (3) is defined by a set of projecting edges (214) of each plate-shaped member (21).

4. The device according to claim 1, wherein said mechanical system includes a slider (24) configured to slide said mechanical system (2) with respect to said base frame (1), a drive unit being present for said slider (24).

5. The device according to claim 1, wherein said plurality of plate-shaped members (21) comprise plate-shaped members (21) made of two different metal materials in such a way that the plate-shaped members (21) made of a first metal material are alternately arranged with respect to the plate-shaped members (21) made of a second metal material.

6. The device according to claim 1, wherein said actuators (23) are divided in two groups, each group being arranged on opposite sides with respect to said plurality of plate-shaped members (21).

7. The device according to claim 1, further comprising a detection system configured to detect a pressure applied by the fingertip of the user, said detection system comprising a pressure sensor (4) positioned on a portion of an upper edge (214) of each plate-shaped member (21) forming said resting area (3), and an acquisition unit connected to each pressure sensor (4).

8. The device according to claim 7, wherein said pressure sensor (4) is a piezoresistive sensor (4).

9. The device according to claim 1, wherein said control unit is a remote unit (61), which controls a microcontroller (62) connected to said actuators (23), said remote unit (61) generating control signals adapted to set a height of each plate-shaped member (21), said microcontroller (62) comprising means for detecting the height of each plate-shaped member (21).

10. The device according to claim 9, wherein said microcontroller (62) comprises one or more control units, each control unit controlling a status of a group of the actuators (23), said control signals being sine waves.

\* \* \* \* \*